United States Patent [19]

Yoon

[11] Patent Number: 4,924,866
[45] Date of Patent: May 15, 1990

[54] WOUND-CLOSING DEVICE

[76] Inventor: InBae Yoon, 2101 Highland Ridge Dr., Phoenix, Md. 21131

[21] Appl. No.: 262,980

[22] Filed: Oct. 26, 1988

[51] Int. Cl.⁵ ............................................. A61B 17/08
[52] U.S. Cl. .................................................... 128/335
[58] Field of Search ..................... 128/335, 334 C, 337

[56] References Cited

U.S. PATENT DOCUMENTS

| | | | |
|---|---|---|---|
| 3,487,836 | 1/1970 | Niebel et al. | 128/335 |
| 4,430,998 | 2/1984 | Harvey et al. | 128/335 |
| 4,526,173 | 7/1985 | Sheehan | 128/335 |
| 4,531,522 | 7/1985 | Bedi et al. | 128/335 |
| 4,535,772 | 8/1985 | Sheehan | 128/335 |
| 4,539,990 | 9/1985 | Stivala | 128/335 |
| 4,624,257 | 11/1986 | Berggren et al. | 128/335 |
| 4,676,245 | 6/1987 | Fukuda | 128/335 |
| 4,702,251 | 10/1987 | Sheehan | 128/335 |

Primary Examiner—Edward M. Coven
Assistant Examiner—Gary Jackson

[57] ABSTRACT

A device for closing wounds is disclosed. The device includes a pair of arms pivotally or movably connected to one another at the inner ends thereof and a pair of skin-engaging members are connected to the arms. The free ends of the skin-engaging members are adapted for piercing the skin in close proximity to a wound. The device is movable from a first, open position wherein the skin-engaging members are separated for placement of the device over a wound to a second, closed position wherein the skin engaging members penetrate the skin adjacent the wound to urge the two edges of a wound together to facilitate healing of the wound. The device includes means for urging the arms to the closed position.

18 Claims, 1 Drawing Sheet

WOUND-CLOSING DEVICE

FIELD OF THE INVENTION

The present invention relates to a device for closing wounds. More particularly, the present invention relates to a mechanical device which is designed to replace either stitches or staples for closing wounds.

BACKGROUND OF THE INVENTION

The most widely used method for closing skin wounds are stitches. Stitches are generally hand-sewn through the skin to close the wound and hold it in place for healing purposes. Many different materials are used for stitches. However, stitches suffer from several disadvantages. First, they are labor intensive since they must be hand-sewn into the individual's skin. Secondly, stitches require a certain degree of manual dexterity on the part of the physician in order to close the wound in such a manner as to minimize the scar which will result. Third, stitches must eventually be removed, usually requiring an additional visit to the doctor's office.

Another method for closing wounds involves the use of staples to close a wound. While staples may be advantageous in certain applications, they require specialized equipment and are difficult to remove from the patient.

Other devices for closing wounds are disclosed in the prior art. For example, in U.S. Pat. No. 3,487,836 (Niebel, et al.) issued on July 16, 1968, there is disclosed a surgical strip stitch wherein an inverted U-shaped member has flexible adhesive strips attached on the extremities thereof for attachment to the skin on either side of a wound which is bridged by the U-shaped member. Skin-engaging projections extend inwardly from each side wall of the U-shaped member and have blunt end portions adapted to clamp the edges of a wound together in a peak therebetween.

Another wound-closure device is disclosed in U S. Pat. Nos. 4,526,173 and 4,702,251 issued on July 2, 1985 and Oct. 27, 1987, respectively. These wound-closure devices comprise a pair of attachment members adapted to be positioned along either side of a wound to be closed. In one embodiment, the device includes a plurality of pins associated with the attachment members for the purpose of urging the dermis on either side of the wound together. In another embodiment, a bridge is provided to hold the two attachment members in abutting alignment to close a wound.

U.S. Pat. No. 4,539,990 (Stivala) issued on Sept. 10, 1985, discloses a sutureless closure system having fabric-backed plates positioned along the side edges of a wound. Arcuate-shaped clips bridge the wound between the plates and contain downwardly extending pins at each end which penetrate the fabric, not the skin, to form a secure anchor for the bridge.

There exists a need in the art for a simple mechanical device which can close a wound. Further, there is a need in the art for a mechanical device for closing wounds which can be removed by the patient, at home, once the wound has healed. Finally, there is a need in the art for a device which will securely close a wound so as to minimize the formation of scar tissue during the wound-healing process.

SUMMARY OF THE INVENTION

The present invention relates to a wound-closing device. The device includes first and second arms pivotally connected to one another at one end thereof for movement between a first, open position and a second, closed position. A first skin-engaging member is connected at one end thereof to an intermediate portion of the first arm and has an inwardly extending free end which is capable of piercing skin. A second skin-engaging member is connected at one end thereof to an intermediate point of the second arm and also has an inwardly extending free end which is capable of piercing skin. The skin-engaging members are shaped such that the free ends are separated by a sufficient distance to span a wound when the arms are in their first, open position. Also, in one embodiment, the shape of the skin-engaging members is such that the free ends are in at least close proximity to one another when the arms are in the second, closed position. The device also includes a means for urging the arms to the second, closed position.

It is a primary object of the present invention to provide a simple, mechanical wound-closure device which can be easily manipulated by a doctor or by other persons with minimal medical experience.

It is a further object of the present invention to provide a wound-closure device which may be customized for closing specialized wounds in order to minimize formation of scar tissue during healing.

It is a still further object of the present invention to provide a wound-closure device which is simple to remove and which can be removed by the patient when the wound is healed.

It is a still further object of the present invention to provide a wound-closure device which is simple and inexpensive to manufacture.

These and other objects of the present invention will be apparent to one of ordinary skill in the art from the detailed description which follows.

DETAILED DESCRIPTION OF THE PREFERRED EMBODIMENTS

Figure 1:
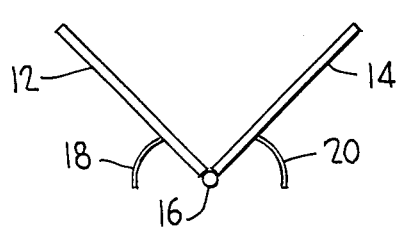
FIG. 1 is a side, elevational view of the wound-closing device in its open position.

Referring now to FIG. 1, there is shown a wound-closing device 10 in accordance with the present invention in its first, open position. The device includes a first arm 12 and a second arm 14 which are pivotally connected at the inner ends thereof by joint 16. The wound-closing device also includes a first skin-engaging member or clip 18 permanently affixed to first arm 12 and a second skin-engaging member or clip 20 permanently affixed to second arm 14. In the first, open position shown in FIG. 1, arms 12 and 14 are pivoted upwardly out of the same plane to the open position wherein the skin-engaging members 18, 20 are separated from one another.

The joint 16 may incorporate a spring of any suitable type therein which may function as an over-center type spring to urge the arms 12, 14 to the open position when they are moved a predetermined distance toward the open position, and also to urge the arms 12, 14 to the closed position when they are moved a predetermined distance toward the closed position. Alternatively, the spring may be constructed to urge the arms 12, 14 to the closed position only.

As a further alternative, the joint 16 may be formed of a malleable material so that the arms 12, 14 can be moved to and held in the open or the closed position.

Figure 2:
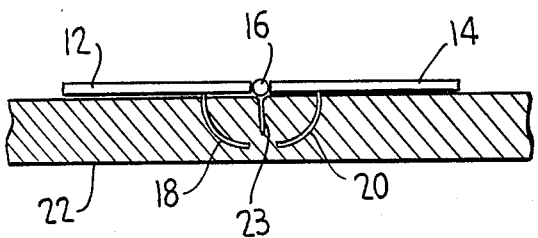
FIG. 2 is a side, elevational view of the wound-closing device in its closed position.

Referring now to FIG. 2, there is shown the wound-closing device of the present invention in its second, closed position. The wound-closing device includes all of the same elements as that of FIG. 1. Skin 22 is pinched together by skin-engaging members 18, 20 to thereby close wound 23. As shown, skin-engaging members or clips 18, 20 penetrate the surface of skin 22 to thereby obtain a good grip on skin 22 near wound 23. Skin-engaging members 18, 20 are preferably shaped so that they extend downwardly and inwardly to pinch together and penetrate skin 22 around wound 23 when the wound-closing device is in its closed position. Preferably, the skin-engaging members are curved downwardly and inwardly as shown in FIGS. 1 and 2. In the second, closed position the free ends of skin-engaging members 18, 20 are at least in close proximity to one another as shown in FIG. 2. The free ends of skin-engaging members 18, 20 may also physically touch one another in the closed position if it is desirable for them to do so. In this manner, skin-engaging members 18, 20 securely and accurately hold the edges of a wound together to promote fast healing with a minimal formation of scar tissue.

Figure 3:
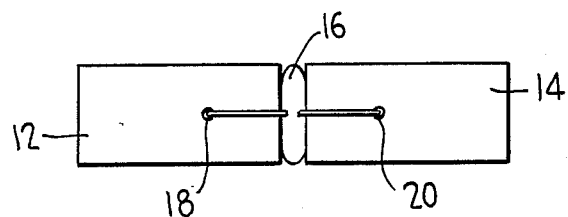
FIG. 3 is a bottom view of the wound-closing device in its closed position.

FIG. 3 shows the bottom portion of the wound-closing device of FIGS. 1 and 2. This view shows the shape of the arms 12, 14 which preferably are planar, generally rectangular members. Also shown are the skin-engaging members 18, 20 in the closed position.

Arms 12, 14 may be fabricated from any suitable thin metal or plastic material, although any other medically acceptable material will suffice. Arms 12, 14 are generally rectangular, planar members in the preferred embodiment to make the device easier to handle during use and operation. Arms 12, 14 are long enough to be easily grasped by a human hand, but may be of limited width such that several wound-closing devices can be used side-by-side to close a large wound and so that a number of wound-closing devices can be placed in close proximity to one another to satisfactorily close a wound, when necessary. In the alternative, arms 12, 14 may be wider, and the device may include more than one skin-engaging member 18, 20 attached to each arm to thereby provide a sufficient grip to close a wound in an acceptable manner, when desired.

The joint 16 may be any medically approved type of spring device or mechanical means for biasing the arms 12, 14 to their closed position. Joint 16 may be constructed so that it urges arms 12, 14 to their open position and to their closed position, as hereinbefore explained. Joint 16 may also be a bendable spring joint and may be fabricated from plastic as an integral part of arms 12, 14. Also, joint 16 could be a spring device which is fabricated separately from arms 12, 14 and then attached by suitable attachment means. The spring force should be sufficient to hold the edges of a wound in close engagement when the wound-closing device is positioned thereon in a closed position to promote wound healing with a minimum of scar tissue.

Alternatively, the joint 16 may comprise a spring device that urges the arms 12, 14 only to their closed position shown in FIG. 2. In this case manual force is necessary to open the arms 12, 14 and hold them in the open position while they are being applied to a would to close it. Release of the arms results in the arms being closed to cause the skin-engaging members 18, 20 to penetrate the skin adjacent the wound, as shown in FIG. 2.

In another embodiment of the invention, the joint 16 may be formed of a stretchable material so that the arms 12, 14 can be grasped and pulled apart from each other. The arms would then be pushed downwardly while pulled apart so that the skin-engaging members 18, 20 would pierce the skin on both sides of the wound. Thereafter, the arms would be released and the skin-engaging members would be pulled toward each other by the resilience of the joint 16 to close the wound. In this embodiment, the skin-engaging members 18, 20 preferably are straight like those shown in FIG. 5 and could be provided with anchoring means of any suitable type to retain them in the skin on both sides of the wound.

Skin-engaging members or clips 18, 20 may be fabricated from any suitable medically acceptable material such as plastic, Teflon or metal, for example. Skin-engaging members 18, 20 may be of various shapes, sizes and orientation depending upon the particular wound to be closed. For example, for larger wounds, skin-engaging members 18, 20 will be larger and will be attached to arms 12, 14 at a point further from joint 16 so that skin-engaging members 18, 20 will span a large wound. To accommodate a smaller wound, skin-engaging members 18, 20 will be smaller in size and will be attached to arms 12, 14 at a point closer to joint 16.

Figure 5:
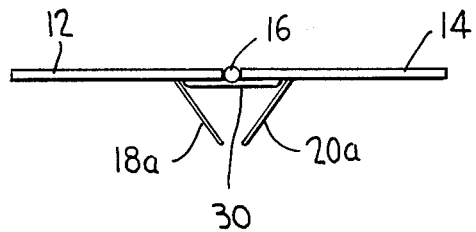
FIG. 5 is a side elevational view of a third embodiment of the wound-closing device in its closed position.

The preferred shape of skin-engaging members 18, 20 is curved as shown in FIGS. 1 and 2. However, other shapes may be used as long as they do not impair the usefulness of the device. For example, an angled member having two straight sections which form an acute angle therebetween can also be used as long as the free ends of skin-engaging members 18, 20 are positioned inwardly for engagement and penetration of the skin around a wound. Also, straight members 18, 20 could be used as shown in FIG. 5.

Free ends of skin-engaging members or clips 18, 20 have a relatively sharp point to provide easy penetration of the skin around the wound. Penetration of the skin is important because it facilitates closure of a wound in an effective manner. Skin-engaging members 18, 20 exert a pinching effect on the skin around the wound in order to bring the edges of the wound into close proximity to thereby facilitate healing and minimize formation of scar tissue. If desired or necessary, the members 18, 20 could be provided with skin-anchoring means of any suitable type.

In the drawings, arms 12, 14 are shown to be in the same plane in their second, closed position. The angle between arms 12, 14 in the closed position, can be varied, however, for different applications. For example, to close a wound in the forearm of a patient, the device can be fabricated such that arms 12, 14, in their closed position, follow the contour of the patient's arm, either by having curved arms 12, 14 or by selecting joint 16 so that arms 12, 14 form an acute angle between one another. The angle on the underside of arms 12, 14 in their closed position is preferably from about 170° to about 190° and more preferably about 180°, although for specific applications, larger or smaller angles may be used. Accordingly, it is contemplated that a wide variety of these wound-closing devices may be fabricated such that the correctly configured device or devices can be chosen for the particular wound to be closed. The devices will vary in both the angle of the arms 12, 14 to one another as well as the size and positioning of skin-engaging members 18, 20, depending upon the type and location of the wound.

In the operation of one embodiment, where the joint 16 has a spring device that urges the arms 12, 14 to the open and the closed positions, the wound-closing device is picked up in the open position as shown in FIG. 1. The wound-closing device is then positioned such that skin-engaging members 18, 20 straddle the wound to be closed. Then, the wound-closing device is lowered to just above the skin with one hand and the other hand is used to grasp on either side of the wound and pinch the skin together to close the wound. Finally, the wound-closing device is moved toward the closed position so that the spring device urges the arms 12, 14 to the closed position wherein skin-engaging members 18, 20 penetrate the skin on either side of the wound and pinch the wound closed. Arms 12, 14 will act as a barrier to help secure the skin and close the wound. As shown in FIG. 2, the skin is pinched by skin-engaging members 18, 20 and impinges against arms 12, 14 as well.

If the spring device urges the arms 12, 14 only to the closed position thereof, in accordance with another embodiment of the invention, the operation would be similar to that hereinbefore described, except that the wound-closing device is picked up in the closed position and manually moved to the open position before applying it to the wound.

To remove the device, one merely grasps the free ends of arms 12, 14 and moves the arms upwardly to open skin-engaging members 18, 20. The wound-closing device is then removed from the site of the wound and may be discarded.

The wound-closing device is sterilized after manufacture and is kept in a sterilized condition until use in any suitable manner in order to minimize the possibility of infection.

Figure 4:
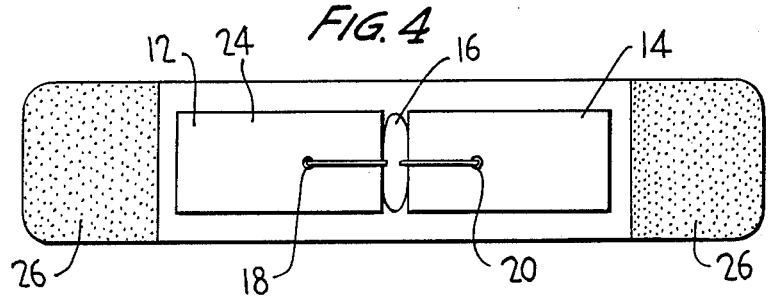
FIG. 4 is a bottom view of a second embodiment of the wound-closing device in its closed position.

A second embodiment of the wound-closing device is shown in FIG. 4 wherein a bandage is attached in any suitable manner to the upper portion of the wound-closing device to provide additional protection to the wound. The bandage includes a wound-covering portion 24, preferably made of gauze or other suitable material and a pair of adhesive end portions 26. Preferably, wound-covering portion 24 is secured in any suitable manner to the tops of arms 12, 14. Adhesive portions 26 provide additional means for retaining the wound-closing device on the patient's skin and wound-covering portion 24 provides additional protection to the wound area from dirt and other contaminating materials. The end portions 26 or other portions of the bandage may be formed of a flexible and resilient material so that the bandage can be stretched before being applied to the wound area to provide an additional closing force to the wound.

In another embodiment, wound-covering portion 24 and/or the bottom portions of arms 12, 14 may include a medicament. The medicament may be any known medical substance which is suitable for the healing of a wound, the prevention of infections or the lessening of pain. Such a medicament could also be appled to the skin-engaging membes 18, 20.

Referring to FIG. 5, a pad 30 or the like under the joint 16 and adjacent portions of the arms 12, 14 could be impregnated or coated with a suitable medicament such as an antiseptic, an anaesthetic, a pain-killing agent or an anti-coagulant. In this embodiment, the skin-engaging members 18a and 20a are shown in a straight configuration as another example of the shape of such members in accordance with this invention.

In still another embodiment of this invention, the bottom surfaces of the arms 12, 14 could be provided with an adhesive of any suitable type to aid in retaining the wound-closing device on the skin in its proper closed position around the wound. This embodiment would provide a dual action in closing the wound, namely, the adhesive and the piercing of the skin around the wound.

The foregoing description of embodiments of the invention has been presented for purposes of illustration and description. It is not intended to be exhaustive or to limit the invention to the precise forms disclosed, and many modifications and variations will be obvious to one of ordinary skill in the art in light of the above teachings. Accordingly, the scope of the invention is to be defined by the claims appended hereto.

I claim:

1. A wound-closing device which comprises:
   first and second arms movably connected to one another at a joint at the inner ends thereof for movement between a first, open position and a second, closing position;
   a first skin-engaging member connected at one end thereof to said first arm and having a free end which is capable of piercing skin;
   a second skin-engaging member connected at one end thereof to said second arm and having a free end which is capable of piercing skin, said skin-engaging members being separated by a sufficient distance to span a wound when said arms are in said first, open position and said free ends being moved closer to one another when said arms are in said second, closed position wherein they pierce the skin surrounding a wound to close it, and
   means for urging movement of said arms about said joint to said second, closed position.

2. A wound-closing device which comprises:
   first and second arms movably connected to one another at a joint at the inner ends thereof for movement between a first, open position and a second, closing position;
   a first skin-engaging member connected at one end thereof to said first arm and having a free end which is capable of piercing skin;
   a second skin-engaging member connected at one end thereof to said second arm and having a free end which is capable of piercing skin, said skin-engaging members being separated by a sufficient distance to span a wound when said arms are in said first, open position and said free ends being moved closer to one another when said arms are in said second, closed position wherein they pierce the skin surrounding a wound to close it, and
   means provided at said joint for urging said arms to said second, closed position.

3. A wound-closing device as claimed in claim 2 wherein said urging means comprises a medically approved spring device.

4. A wound-closing device as claimed in claim 2 wherein said first and second arms are substantially planar.

5. A wound-closing device as claimed in claim 4 wherein said skin-engaging members extend downwardly and inwardly from said arms.

6. A wound-closing device as claimed in claim 4 wherein said arms define an angle of about 170° to about 190° when said arms are in said second, closed position.

7. A wound-closing device as claimed in claim 4 further comprising a bandage means attached to said arms for covering the closed wound.

8. A wound-closing device as claimed in claim 7 wherein said bandage means comprises at least one adhesive surface for retaining said bandage means on skin.

9. A wound-closing device as claimed in claim 7 wherein said bandage means further comprises a beneficial, body-treating composition in association therewith.

10. A wound-closing device as claimed in claim 7 wherein said bandage means comprises a flexible and resilient portion so that it can be stretched before applying it to the wound.

11. A wound-closing device as claimed in claim 2 further comprising at least two skin-engaging members attached to each of said first and second arms.

12. A wound-closing device which comprises:
first and second arms movably connected to one another at a joint at the inner ends thereof for movement between a first, open position and a second, closing position;
a first skin-engaging member connected at one end thereof to said first arm and having a free end which is capable of piercing skin;
a second skin-engaging member connected at one end thereof to said second arm and having a free end which is capable of piercing skin, said skin-engaging members being separated by a sufficient distance to span a wound when said arms are in said first, open position and said free ends being moved closer to one another when said arms are in said second, closed position wherein they pierce the skin surrounding a wound to close it, and
means for urging said arms to said second, closed position, said urging means also urging said arms to said open position when they are moved a predetermined distance toward said open position.

13. A wound-closing device which comprises:
first and second arms pivotally connected to one another at a joint at the inner ends thereof for movement between a first, open position and a second, closing position;
a first skin-engaging member connected at one end thereof to said first arm and having a free end which is capable of piercing skin;
a second skin-engaging member connected at one end thereof to said second arm and having a free end which is capable of piercing skin, said skin-engaging members being separated by a sufficient distance to span a wound when said arms are in said first, open position and said free ends being moved closer to one another when said arms are in said second, closed position wherein they pierce the skin surrounding a wound to close it, and
means for urging said arms to said second, closed position.

14. A wound-closing device as claimed in claim 13 wherein said joint is formed of a stretchable material.

15. A wound-closing device as claimed in claim 13 wherein said joint is formed of a malleable material.

16. A wound-closing device as claimed in claim 13 wherein said arms further comprise a beneficial, body-treating composition in association therewith.

17. A wound-closing device as claimed in claim 13 wherein said skin-engaging members further comprise a beneficial, body-treating composition in association therewith.

18. A wound-closing device as claimed in claim 13 wherein each of said arms comprises an adhesive surface for retaining it on the skin when in the closed position.

* * * * *